United States Patent [19]

Rodgers et al.

[11] Patent Number: 5,716,935
[45] Date of Patent: Feb. 10, 1998

[54] USE OF ANTIOTENSIN II ANALOGS IN TISSUE REPAIR

[75] Inventors: Kathleen Elizabeth Rodgers, Long Beach; Gere Stodder Dizerega, Pasadena, both of Calif.

[73] Assignee: University of Southern California, Los Angeles, Calif.

[21] Appl. No.: 594,117

[22] Filed: Jan. 31, 1996

Related U.S. Application Data

[63] Continuation of Ser. No. 126,370, Sep. 24, 1993, abandoned.

[51] Int. Cl.$^6$ ............................ A61K 38/00; C07K 5/00; C07K 7/00
[52] U.S. Cl. .......................... 514/16; 514/15; 514/17; 530/328; 530/329
[58] Field of Search ........................ 514/15, 16, 17; 530/328, 329

[56] References Cited

U.S. PATENT DOCUMENTS 5,015,629   5/1991   diZerega ........................ 514/16

OTHER PUBLICATIONS

Erspamer et al. Experientia 3(1979) 1132–1133.
Dayhoff Atlas of Protein Sequence and Structure 1972 vol. 5.
Bell, L., et al., Influence of the Angiotensin System on Endothelial and Smooth Muscle Cell Migration, *Am. J. Pathol.* vol., 137, No. 1, pp. 7–12 (Jul. 1990).
Bell, L., et al., Autocrine Angiotensin System Regulation of Bovine Aortic Endothelial Cell Migration and Plasminogen Activator Involves Modulation of Proto–oncogene pp. $60^{c-src}$ Expression, *J. Clin. Invest.*, vol. 89, pp. 315–320 (Jan. 1992).
Bell, L., et al., Autocrine Angiotensin System Regulation of Bovine Aortic Endothelial Cell Migration and Plasminogen Activator Involves Modulation of Proto–oncogene $pp60^{c-src}$ Expression, *J. Clin. Invest.*, vol. 89, pp. 315–320 (Jan. 1992).
Berk, B.C., et al., Angiotensin II–Induced Vascular Smooth Muscle Cell Hypertrophy: PDGF A–Chain Mediates the Increase in Cell Size, *J. Cell. Physiol.*, vol. 154, pp. 368–380 (1993).
Campbell–Boswell, M., et al., Effects of Angiotensin II and Vasopressin on Human Smooth Muscle Cells in Vitro, *Exp. Mol. Pathol.*, vol. 35, pp. 265–276 (1981).
Capron, L., et al., Effect of Ramipril, an Inhibitor of Angiotensin Converting Enzyme, on the Response of Rat Thoracic Aorta to Injury with a Balloon Catheter, *J. Cardiovasc. Pharmacol.*, vol. 18, No. 2, pp. 207–211 (1991).
Daemen, M.J.A.P., et al., Angiotensin II Induces Smooth Muscle Cell Proliferation in the Normal and Injured Rat Arterial Wall, *Circulation Research*, vol. 68, No. 2, pp. 450–456 (Feb. 1991).

Dzau, V.E., et al., Molecular Mechanism of Angiotensin in the Regulation of Vascular and Cardiac Growth, *J. Mol. Cell. Cardiol.*, vol. 21 (Supplement III), S.7 (1989).
Emmett, N., et al, Effect of Saralasin (Angiotensin II Antagonist) on 3T3 Cell Growth and Proliferation, *J. Cell. Biol.*, vol. 103; 171(Abst.) (1986).
Fernandez, L.A., et al., Neovascularization Produced By Angiotensin II, *J. Lab. Clin. Med.*, vol. 105, No. 2, pp. 141–145 (Feb. 1985).
Geisterfer, A.A.T., et al., Angiotensin II Induces Hypertrophy, not Hyperplasia, of Cultured Rat Aortic Smooth Muscle Cells, *Circulation Research*, vol. 62, No. 4, pp. 749–756 (Apr. 1988).
Gibbons, G.H., et al., Vascular Smooth Muscle Cell Hypertrophy vs. Hyperplasia. Autocrine Transforming Growth Factor–$\beta_1$ Expression Determines Growth Response to Angiotensin II, *J. Clin. Invest.*, vol. 90, pp. 456–461 (Aug. 1992).
Greenhalgh, D.G., PDGF and FGF Stimulate Would Healing in the Genetically Diabetic Mouse, *Am. J. Pathol.*, vol. 136, No. 6, pp. 1235–1246 (Jun. 1990).
Grotendorst, G.R., et al., Stimulation of Granulation Tissue Formation by Platelet–derived Growth Factor in Normal and Diabetic Rats, *J. Clin. Invest.*, vol. 76, pp. 2323–2329 (Dec. 1985).
Harding, J.W., et al., "The Effects of the Aminopeptidase Inhibitors Amastatin and Bestatin on Angiotensin–evoke Neuronal Activity in Rat Brain", *Brain Research*, 424:299–304 (1987).
Hunt, T.K., et al., Coagulation and Macrophage Stimulation of Angiogenesis and Wound Healing, *The Surgical Wound*, pp. 1–18, ed. F. Dineen & G. Hildrick–Smith (Lea & Febiger, Philadelphia 1981).
Israel, A., et al., "Quantitative Determination of Angiotensin II Binding Sites in Rat Brain and Pituitary Gland by Autoradiography", *Brain Research*, 322:341–345 (1984).
Kawahara, Y., et al., Angiotensin II Induces Expression of the c–fos Gene Through Protein Kinase C Activation and Calcium Ion Mobilization in Cultured Vascular Smooth Muscle Cells, *Biochemical and Biophysical Research Communications*, vol. 150, No. 1, pp. 52–59 (Jan. 15, 1988).
Kimura, B., et al., Changes in Skin Angiotensin II Receptors in Rats During Wound Healing, *Biochemical and Biophysical Research Communications*, vol. 187, No. 2, pp. 1083–1090 (Sep. 16, 1992).

(List continued on next page.)

*Primary Examiner*—Avis M. Davenport
*Attorney, Agent, or Firm*—Knobbe Martens Olson & Bear, LLP

[57] ABSTRACT

Analogs of angiotensin II are useful in accelerating wound healing. These analogs form the basis of compositions useful for accelerating wound healing, in which the active agent is present in an amount effective to accelerate wound healing. Preferably, the compositions are in the form of matrical or micellar solutions.

20 Claims, 3 Drawing Sheets

OTHER PUBLICATIONS

Le Noble, F.A.C., et al., Angiotensin II Stimulates Angiogenesis in the Chorio-allantoic Membrane of the Chick Embryo, Eur. J. Pharmacol., vol. 195, pp. 305-306 (1991).

Lynch, S.E., et al., Growth Factors in Would Healing. Single and Synergistic Effects on Partial Thickness Porcine Skin Wounds, J. Clin. Invest., vol. 84, pp. 640-646 (Aug. 1989).

Mendelsohn, F.A.O., et al., "Autoradiographic Localtion of Angiotensin II Receptors in Rat Brain", Proc. Natl. Acad. Sci. USA, vol. 81, pp. 1575-1579 (Mar., 1984).

Mustoe, T.A., et al., Accelerated Healing of Incisional Wounds in Rats Induced by Transforming Growth Factor-$\beta$, Science, vol. 237, pp. 1333-1336 (Sep. 11, 1987).

Naftilan, A.J., et al., Induction of Platelet-derived Growth Factor A-Chain and c-myc Gene Expressions by Angiotensin II in Cultured Rat Vascular Smooth Muscle Cells, J. Clin. Invest., vol. 83, pp. 1419-1424 (Apr., 1989).

Naftilan, A.J., "The Role of Angiotensin II in Vascular Smooth Muscle Cell Growth", J. of Cardiovascular Pharm., 20 (Suppl. 1):S37-S40 (1992).

Nakahara, K., et al., Identification of Three Types of PDGF-A Chain Gene Transcripts in Rabbit Vascular Smooth Muscle and Their Regulated Expression During Development and By Angiotensin II, Biochemical and Biophysical Research Communications, vol. 184, No. 2, pp. 811-818 (Apr. 30, 1992).

Osterrieder, W., et al., Role of Angiotensin II in Injury-Induced Neointima Formation in Rats, Hypertension, Supplement II, vol. 18, No. 4, pp. II-60—II-64 (Oct. 1991).

Paquet, J., et al., Angiotensin II-induced Proliferation of Aortic Myocytes in Spontaneously Hypersensitive Rats, J. Hypertens., vol. 8, No. 6, pp. 565-572 (1990).

Pierce, G.F., et al., In Vivo Incisional Would Healing Augmented By Platelet-derived Growth Factor and Recombinant c-sis Gene Homodimeric Proteins, J. Exp. Med., vol. 167, pp. 974-987 (Mar. 1988).

Powell, J.S., et al., Inhibitors of Angiotensin-Converting Enzyme Prevent Myointimal Proliferation After Vascular Injury, Science, vol. 245, pp. 186-188 (Jul. 14, 1989).

Powell, J.S., et al., The Proliferative Response to Vascular Injury Is Suppressed by Angiotensin-Converting Enzyme Inhibition, J. Cardiovasc. Pharmacol., vol. 16, Suppl. 4, pp. S42-S49 (1990).

Printz, M.P., et al., Evidence for the Presence of Hydrogen-Bonded Secondary Structure in Angiotensin II in Aqueous Solution, Proc. Nat. Acad. Sci., vol. 69, No. 2, pp. 378-382 (Feb. 1972).

Regoli, D., et al., Role of the N-terminal Amino Acid for the Biological Activities of Angiotensin and Inhibitory Analogues, Can. J. Physio. Pharmacol., vol. 52, pp. 39-49 (1974).

Regoli, D., et al., "Pharmacology of Angiotensin", Pharmacological Reviews, (Williams & Wilkins Co. 1974).

Schelling, P., et al., Effects of Angiotensin II and Angiotensin II Antagonist Saralasin on Cell Growth and Renin in 3T3 and SV3T3 Cells, J. Cell. Physiol., vol. 98, pp. 503-514 (1979).

Stouffer, G.A., et al., Angiotensin II-Induced Mitogenesis of Spontaneously Hypertensive Rat-Derived Cultured Smooth Muscle Cells Is Dependent on Autocrine Production of Transforming Growth Factor-$\beta$, Circ. Res., vol. 70, pp. 820-828 (1992).

Taubman, M.B., et al., Angiotensin II Induces c-fos mRNA in Aortic Smooth Muscle. Role of $Ca^{2+}$Mobilization and Protein Kinase C Activation, J. Biol. Chem., vol. 264, No. 1, pp. 526-530, (Jan. 5, 1989).

Temizer, et al., "Induction of Heparin-binding Epidermal Growth Factor-Like Growth Factor mRNA by Phorbol Ester and Angiotensin II in Rat Aortic Smooth Muscle Cells", J. of Biol. Chemistry, 267:24892-24896 (Dec. 5, 1992).

Viswanathan, M., et al., Expression of Angiotensin II $AT_2$ Receptors in the Rat Skin During Experimental Wound Healing, Peptides, vol. 13, pp. 783-786 (1992).

Wolf, G., et al., Angiotensin II Stimulates the Proliferation and Biosynthesis of Type I Collagen in Cultured Murine Mesangial Cells, Am. J. Pathol., vol. 140, No. 1, pp. 95-107 (Jan. 1992).

Wolf, G., et al., Intracellular Signaling of Transcription and Secretion of Type IV Collagen After Angiotensin II-Induced Cellular Hypertrophy in Cultured Proximal Tubular Cells, Cell Regulation, vol. 2, pp. 219-227 (Mar. 1991).

Zhou, G., et al., Angiotensin II-Mediated Stimulation of Collagen Synthesis in Cultured Cardiac Fibroblasts, FASEB J., vol. 6, pp. A1914 (1992).

USE OF ANTIOTENSIN II ANALOGS IN TISSUE REPAIR

This application is a continuation of U.S. patent application No. 08/126,370, filed Sep. 24, 1993, now abandoned.

BACKGROUND OF THE INVENTION

This invention relates generally to the fields of biochemistry and medicine. More particularly, the present invention relates to methods and substances for use in accelerating the growth or healing of tissue.

Wounds (i.e., lacerations or openings) in mammalian tissue result in tissue disruption and coagulation of the microvasculature at the wound face. Repair of such tissue represents an orderly, controlled cellular response to injury. All soft tissue wounds, regardless of size, heal in a similar manner. Tissue growth and repair are biologic systems wherein cellular proliferation and angiogenesis occur in the presence of an oxygen gradient. The sequential morphological and structural changes which occur during tissue repair have been characterized in great detail and have in some instances been quantified [Hunt, T. K. et al., "Coagulation and macrophage stimulation of angiogenesis and wound healing," in *The surgical wound*, pp. 1–18, ed. F. Dineen & G. Hildrick-Smith (Lea & Febiger, Philadelphia: 1981)].

The cellular morphology consists of three distinct zones. The central avascular wound space is oxygen deficient, acidotic and hypercarbic, and has high lactate levels. Adjacent to the wound space is a gradient zone of local anemia (ischemia) which is populated by dividing fibroblasts. Behind the leading zone is an area of active collagen synthesis characterized by mature fibroblasts and numerous newly-formed capillaries (i.e., neovascularization). While this new blood vessel growth (angiogenesis) is necessary for the healing of wound tissue, angiogenic agents are in general unable to fulfill the long-felt need of providing the additional biosynthetic effects of tissue repair. Despite the need for more rapid healing of wounds (i.e., severe burns, surgical incisions, lacerations and other trauma), to date there has been only limited success in accelerating wound healing with pharmacological agents.

U.S. Pat. No. 5,015,629 to DiZerega (the entire disclosure of which is hereby incorporated by reference) describes a method for increasing the rate of healing of wound tissue, comprising the application to such tissue of angiotensin II (ATII) in an amount which is sufficient for said increase. The application of angiotensin II to wound tissue significantly increases the rate of wound healing, leading to a more rapid re-epithelialization and tissue repair. The term angiotensin II refers to an octapeptide present in humans and other species having the sequence Asp-Arg-Val-Tyr-Ile-His-Pro-Phe [SEQ ID NO:1]. Angiotensin II is a known pressor agent and is commercially available.

Despite the utility of angiotensin II in accelerating wound healing, there remains a need for additional agents which are useful in promoting wound healing.

SUMMARY OF THE INVENTION

The present invention relates to the use of analogs of angiotensin II in wound healing. Analogs of interest in accordance with the present invention have the general formula

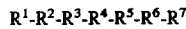   I in which $R^1$ is a group of formula

, wherein X is H or a one to three peptide group and $R^A$ and $R^B$ together form a peptide bond labile to aminopeptidase A cleavage;

$R^2$ is selected from the group consisting of Val, Ala, Leu, Ile, Gly, Pro, Aib, Acpc and Tyr;

$R^3$ is selected from the group consisting of Tyr, Thr, Ser and azaTyr;

$R^4$ is selected from the group consisting of Ile, Ala, Leu, Val and Gly;

$R^5$ is His or Arg;

$R^6$ is Pro or Ala; and $R^7$ is selected from the group consisting of Phe, Phe(Br) and Tyr, excluding the sequence Asp-Arg-Val-Tyr-Ile-His-Pro-Phe [SEQ ID NO:2].

These analogs form the basis of compositions useful for accelerating wound healing, the compositions comprising at least one compound of general formula I in an amount effective to accelerate wound healing. Preferably, the compositions are in the form of matrical or micellar solutions.

DETAILED DESCRIPTION OF THE INVENTION

Figure 1:
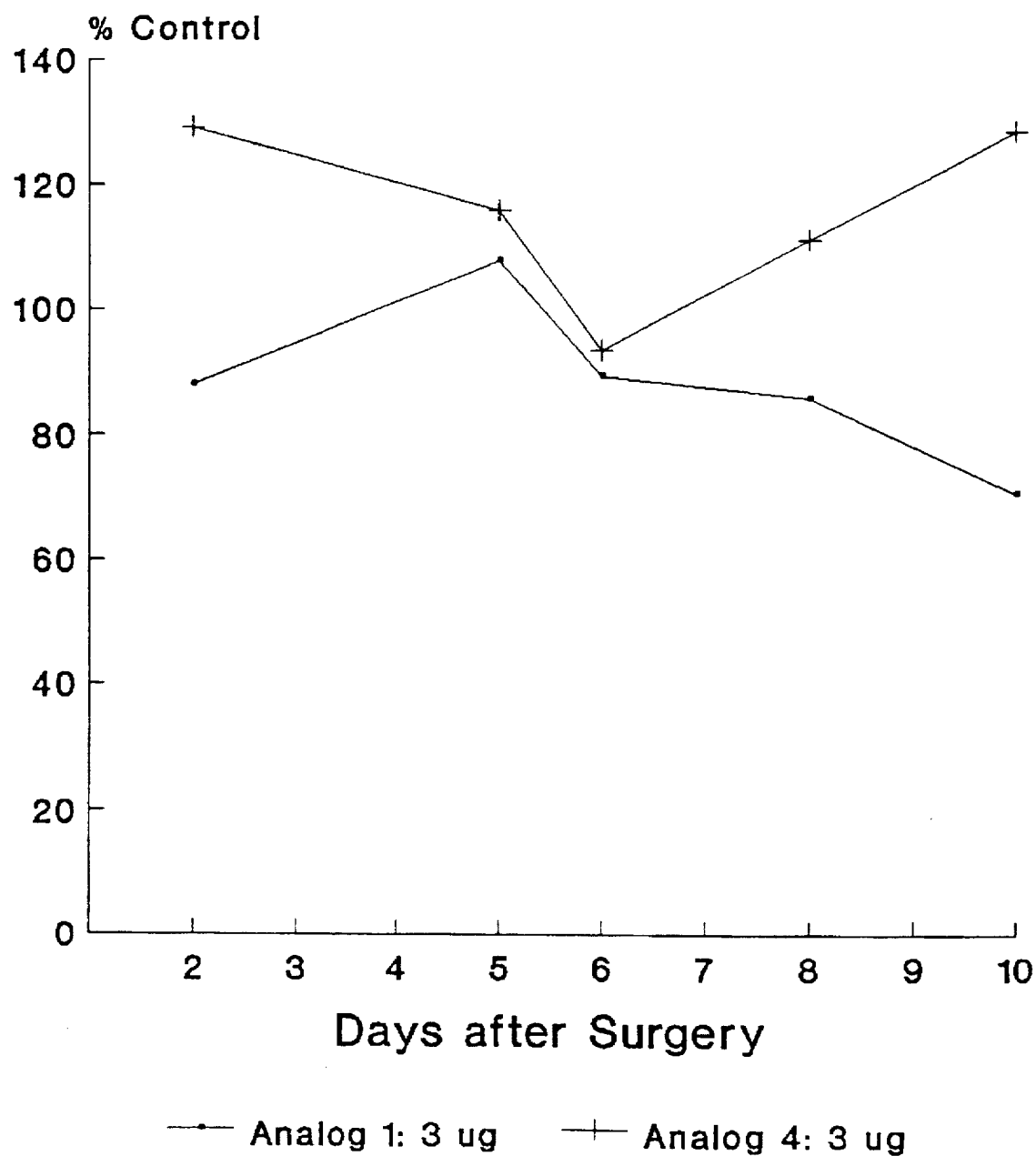

Pursuant to the present invention, wound healing in mammalian tissue is promoted through the use of a composition comprising an effective amount of at least one compound of the general formula I. The active agent of general formula I is generally administered in a matrical or micellar solution and is effective in accelerating re-epithelialization and tissue repair even in very low concentrations.

The compounds employed in the compositions of the present invention are a discrete subset of analogs of angiotensin II. Angiotensin II is one of the most potent vasoconstrictors known, causing constriction of the small arteries that branch to form the capillaries, i.e., the arterioles. The biological formation of angiotensin is initiated by the action of renin on the plasma substrate angiotensinogen. The substance so formed is a decapeptide called angiotensin I which is converted to angiotensin II by the converting enzyme angiotensinase that removes the C-terminal His-Leu residues from angiotensin I.

Recent studies have shown that the vasoactive product of the renin-angiotensin system, angiotensin II (AII), increases the release of growth factors, mitogenesis, chemotaxis and the release of extracellular matrices of cultured cells that are involved in wound repair [Dzau V. E. et al. (1989) Molecular mechanism of angiotensin in the regulation of vascular and cardiac growth. J Mol Cell Cardiol 21 (Supple III):S7; Berk, B C et al. (1989) Angiotensin II stimulated protein synthesis in cultured vascular smooth muscle cells. Hypertension 13:305–14; Kawahara, Y, et al. (1988) Angiotensin II induces expression of the c-fos gene through protein kinase C activation and calcium ion mobilization in cultured vascular smooth muscle cells. BBRC 150:52–9; Naftilan, A J et al. (1989) Induction of platelet-derived growth factor A-chain and c-myc gene expressions by angiotensin II in cultured rat vascular smooth muscle cells. J Clin Invest 83:1419–24; Taubman, M B et al. (1989) Angiotensin II induces c-fos mRNA in aortic smooth muscle. Role of $Ca^{2+}$mobilization and protein kinase C activation. J Biol Chem 264:526–530; Nakahara, K et al. (1992) Identification of three types of PDGF-A chain gene transcripts in rabbit vascular smooth muscle and their regulated expression during development and by angiotensin II. BBRC 184:811–8; Stouffer GA and GK Owens. (1992) Angiotensin II induced mitogenesis of spontaneously hypertensive rat derived cultured smooth muscle cells is dependent on autocrine production of transforming growth factor-β. Circ Res 70:820;

Wolf, G et al. (1992) Angiotensin II stimulates the proliferation and biosynthesis of type I collagen in cultured murine mesangial cells. Am J Pathol 140:95–107; Bell, L and J A Madri (1990) Influence of the angiotensin system on endothelial and smooth muscle cell migration. Am J Pathol 137:7–12]. In addition, AII was shown to be angiogenic in rabbit corneal eye and chick chorioallantoic membrane models (Fernandez, L A et al. (1985) Neovascularization produced by angiotensin II. J Lab Clin Med 105:141; LeNoble, F A C et al. (1991) Angiotensin II stimulates angiogenesis in the chorio-allantoic membrane of the chick embryo. Eur J Pharmacol (1991) 195:305–6]. Therefore, AII may accelerate wound repair through increased neovascularization, growth factor release, reepithelialization and production of extracellular matrix. Through an increase in the flow of blood and nutrients to an injured tissue, AII may increase the rate of wound repair. AII may also accelerate wound repair through the generation of growth factors at the site of injury. Exogenous addition of growth factors has been shown to accelerate wound repair through a variety of mechanisms [Grotendorst, G R et al. (1985) Stimulation of granulation tissue formation by platelet-derived growth factor in normal and diabetic rats. J Clin Invest 76:2323–9; Mustoe, TA et al. (1987) Accelerated healing of incisional wounds in rats induced by transforming growth factor-β. Science 237:1333–5; Pierce, G F et al. (1988) In vivo incisional wound healing augmented by platelet-derived growth factor and recombinant c-sis gene homodimeric proteins. J Exp Med 167:974–87; Lynch, S E et al. (1989) Growth factors in wound healing. J Clin Invest 84:640–6; Greenhalgh, D G et al. (1990) PDGF and FGF stimulate wound healing in the genetically diabetic mouse. Am J Pathol 136:1235–46]. Recent studies showed that AII increased neointima formation in the carotid artery and aorta after injury [Powell, J S et al. (1989) Inhibitors of angiotensin-converting enzyme prevent myointimal proliferation after vascular injury. Science 245:186–8; Powell, J S et al. (1991) The proliferative response to vascular injury is suppressed by converting enzyme inhibition. J Cardiovasc Pharmacol 16 (suppl 4):S42–9; Capron, L et al. (1991) Effect of ramipril, an inhibitor of angiotensin converting enzyme, on the response of rat thoracic aorta to injury with a balloon catheter. J Cardiovasc Pharmacol 18:207–11; Osterriedes, W et al. (1991) Role of angiotensin II injury-induced neointima formation in rats. Hypertension 18: Suppl II60–64; Daemen, M J A P et al. (1991) Angiotensin II induces smooth muscle cell proliferation in the normal and injured rat arterial wall. Circ Res 68:450–6]. As a result of these observations, studies were conducted to determine the mechanism by which endogenous AII may induce intimal hyperplasia. AII was shown to act as a mitogen for smooth muscle cells, fibroblasts and endothelial cells [Schelling, P et al. (1979) Effects of angiotensin II and angiotensin II antagonist saralysin on cell growth and renin in 3T3 and SV3T3 cells. J Cell Physiol 98:503–13; Campbell-Boswell, M and A L Robertson. (1981) Effects of angiotensin II and vasopressin on human smooth muscle cells in vitro. Exp Mol Pathol 35:265–76; Emmett, N et al. (1986) Effect of saralasin (angiotensin II antagonist) on 3T3 cell growth and proliferation. J Cell Biol 103:171 (Abst); Paquet, JL et al. (1990) Angiotensin II-induced proliferation of aortic myocytes in spontaneously hypertensive rats. J Hypertens 8:565–72; Dzau et al, supra]. AII also increased the protein content and size of vascular smooth muscle cells [Berk et al. (1989), supra; Geisterfer, A A T et al. (1988) Angiotensin II induces hypertrophy, not hyperplasia, of cultured rat aortic smooth muscle cells. Circ Res 62:749–56]. Studies showed that AII increases the release of growth factors of various types, including PDGF, heparin-binding EGF and transforming growth factor-β (TGFβ), and growth-related proto-oncogenes from smooth muscle cells, endothelial cells and cardiac fibroblasts [Kawahara et al. (1988), supra; Naftilan, A J (1992) The role of angiotensin II in vascular smooth muscle cell growth. J Cardiovas Pharmacol 20:S37–40; Naftilan et al. (1989), supra; Taubman et al. (1989), supra; Nakahara et al. (1992), supra; Temizer et al. (1992), supra; Gibbons, G H et al. (1992) Vascular smooth muscle cell hypertrophy vs hyperplasia. Autocrine transforming growth factor-beta 1 expression determines growth response to angiotensin II. J Clin Invest 90:456–61; Bell, L et al. (1992) Autocrine angiotensin system regulation of bovine aortic endothelial cell migration and plasminogen activator involves modulation of proto-oncogene pp60c-src expression. J Clin Invest 89:315–20; Stouffer and Owens (1992), supra]. The hypertrophy of vascular smooth muscle cells by AII was mediated through PDGF [Berk, B C and G N Rao. (1993) Angiotensin II-induced vascular smooth muscle cell hypertrophy: PDGF A-chain mediates the increase in size. J Cell Physiol 154:368–80].

Therefore, it is conceivable that AII acts to accelerate wound repair through increasing the levels of these growth factors in the wound tissue. Additionally, AII was shown to stimulate collagen synthesis thereby suggesting a role for this factor in extracellular matrix formation [Wolf, G et al. (1991) Intracellular signalling of transcription and secretion of type IV collagen after angiotensin II-induced cellular hypertrophy in cultured proximal tubular cells. Cell Reg 2:219–27; Wolf et al. (1992), supra; Zhou, G et al. (1992) Angiotensin II mediated stimulation of collagen synthesis in cultured cardiac fibroblasts. FASEB J 6:A1914]. Wound repair also involves chemotaxis of the necessary cell types into the wound bed. AII was also shown to induce the migration of endothelial cells and smooth muscle cells in vitro [Bell and Madri (1990), supra].

Recent studies also indicate that expression of AII receptors increases during the process of wound repair [Viswanathan, M, and J M Saavedra (1992) Expression of Angiotensin II AT$_2$ Receptors in the Rat Skin During Experimental Wound Healing. Peptides 13:783–6; Kimura, B et al. (1992) Changes in skin angiotensin II receptors in rats during wound healing. BBRC 187:1083–1090]. These increases, along with evidence of an increase in the local production of AII at the site of repair, suggests that AII may play a key role in the process of wound repair.

Surprisingly, it has now been discovered that many heretofore known angiotensin II analogs having increased binding strength to angiotensin receptors and/or prolonged activity relative to the native human angiotensin II are not suitable for use in accordance with the present invention. In particular, various analogs which are partially or completely resistant to the action of aminopeptidases and are pharmacologically useful as vasopressors [Printz, M. P. et al., Proc. Nat. Acad. Sci. USA 69:378 (1972); Regoli, D. et al., Can. J. Physiol. Pharmacol. 52:39 (1974)] simply are not suitable for use in accordance with the present invention.

Analogs of particular interest in accordance with the present invention are those of the general formula I

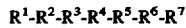

in which $R^1$ is a group of formula

wherein X is H or a one to three peptide group and $R^A$ and $R^B$ together form a peptide bond labile to aminopeptidase A cleavage;

$R^2$ is selected from the group consisting of Val, Ala, Leu, Ile, Gly, Pro, Aib, Acpc and Tyr;

$R^3$ is selected from the group consisting of Tyr, Thr, Ser and azaTyr;

$R^4$ is selected from the group consisting of Ile, Ala, Leu, Val and Gly;

$R^5$ is His or Arg;

$R^6$ is Pro or Ala; and $R^7$ is selected from the group consisting of Phe, Phe(Br) and Tyr, excluding the sequence Asp-Arg-Val-Tyr-Ile-His-Pro-Phe [SEQ ID NO:1]. $R^A$ is suitably selected from Asp, Glu, Ash, Acpc (1-aminocyclopentane carboxylic acid), Ala, Me$^2$Gly, Pro, Bet, Glu(NH$_2$), Gly, Asp(NH$_2$) and Suc. $R^B$ is suitably selected from Lys, Arg, Ala and Orn. Preferred combinations for $R^A$ and $R^B$ are Asp-Lys, Glu-Arg and Glu-Lys.

A preferred class of angiotensin II analogs has the formula

H-R$^A$-R$^B$-R$^2$-Tyr-R$^4$-His-Pro-Phe      [SEQ ID NO:2]

wherein $R^A$, $R^B$, $R^2$ and $R^4$ are as previously defined. Particularly preferred are those analogs wherein $R^A$ and $R^B$ are Asp-Lys, Glu-Arg or Glu-Lys.

In the above formulas, the standard three-letter abbreviations for amino acid residues are employed. In the absence of an indication to the contrary, the L-form of the amino acid is intended. Other residues are abbreviated as follows:

| | |
|---|---|
| Me$^2$Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
azaTyr | aza-α'-homo-L-tyrosyl |
| Acpc | 1-aminocyclopentane carboxylic acid |
| Aib | 2-aminoisobutyric acid |

It has been suggested that AII and its analogs adopt either a gamma or a beta turn [Regoli, D. et al. (1974) Pharmacology of Angiotensin. Pharmacological Reviews 26:69]. In general, it is believed that neutral side chains in positions $R^2$, $R^4$ and $R^6$ may be involved in maintaining the appropriate distance between the active groups in positions $R^3$, $R^5$ and $R^7$ primarily responsible for binding to receptors and/or intrinsic activity. Hydrophobic side chains in positions $R^2$, $R^4$ and $R^7$ may also play an important role on the whole conformation of the peptide and/or contribute to formation of a hypothetical hydrophobic pocket.

For purposes of the present invention, it is believed that $R^2$ may be involved in the formation of linear or non-linear hydrogen bonds with $R^4$ (in the gamma turn model) or $R^5$ (in the beta turn model). $R^2$ would also participite in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^2$ may suitably be selected from Val, Ala, Leu, Ile, Gly, Pro, Aib, Acpc and Tyr.

With respect to $R^3$, conformational analyses have suggested that the side chain in this position (as well as in $R^2$ and $R^4$) contribute to a hydrophobic cluster believed to be essential for occupation and stimulation of receptors. Thus, $R^3$ is preferably selected from Tyr, Thr, Ser and azaTyr. In this position, Tyr is particularly preferred as it may form a hydrogen bond with the receptor site capable of accepting a hydrogen from the phenolic hydroxyl [Regoli et al., supra].

In position $R^4$, an amino acid with a β aliphatic or alicyclic chain is particularly desirable. Therefore, while Gly is suitable in position $R^4$, it is preferred that the amino acid in this position be selected from Ile, Ala, Leu and Val.

In the analogs of particular interest in accordance with the present invention, $R^5$ is His or Arg. The unique properties of the imidazole ring of histidine (e.g., ionization at physiological pH, ability to act as proton donor or acceptor, aromatic character) are believed to contribute to its particular utility as $R^5$. For example, conformational models suggest that His may participate in hydrogen bond formation (in the beta model) or in the second turn of the antiparallel structure by influencing the orientation of $R^6$. Similarly, it is presently considered that $R^6$ should be Pro in order to provide the most desirable orientation of $R^7$. In position $R^7$, both a hydrophobic ring and an anionic carboxyl terminal appear to be particularly useful in binding of the analogs of interest to receptors; therefore, Tyr and especially Phe are preferred for purposes of the present invention.

Specific analogs of particular interest include the following:

| | | |
|---|---|---|
| Analog 1 | Asp—Arg—Val—Tyr—Val—His—Pro—Phe | SEQ ID NO:3 |
| Analog 2 | Asn—Arg—Val—Tyr—Val—His—Pro—Phe | SEQ ID NO:4 |
| Analog 3 | Ala—Pro—Gly—Asp—Arg—Ile—Tyr—Val—His—Pro—Phe | SEQ ID NO:5 |

According to the method of the invention, the angiotensin II analogs of the invention are applied to wound tissue in amounts sufficient to increase the healing rate of tissue. These compounds can significantly accelerate the rate of healing at nanogram levels both in vitro and in vivo. Specifically, the rate of neovascularization in wound tissue can be increased when a solution containing nanogram amounts per milliliter of at least one of the compounds of the invention is applied to the tissue, and a significant increase in capillary proliferation can be provided when a solution containing microgram amounts per milliliter is employed.

The compounds of the invention may be applied in a variety of solutions. Suitable solutions for use in accordance with the present invention are sterile, dissolve sufficient amounts of the peptide, and are not harmful to wound tissue. In this regard, the compounds of the present invention are very stable but are hydrolyzed by strong acids and bases. The compounds of the present invention are soluble in organic solvents and in aqueous solutions at pH 5–8.

Any type of application means may be employed which permits the influx of the active agents into the tissue over a period of time. For example, an aqueous solution could be applied to the wound tissue through a gauze bandage or strip, or such a solution could be formulated so that a timed perfusion may be obtained (using, e.g., liposomes, ointments, micelles, etc). Methods for the production of these formulations with the compounds of the present invention are apparent to those of ordinary skill in the art. The particular concentration of active agent employed is not critical, as the tissue-repairing effect is present even when the compounds are present in nanogram quantities.

Preferably, a matrical or miceliar solution is employed with the active agent present in a concentration of at least 30 micrograms per milliliter. A particular matrical solution which has been used to advantage in the described examples is a semi-solid polyethylene glycol polymer sold under the trademark Hydron by Hydro Med Sciences, New Brunswick, N.J. Another preferred solution is a micellar solution sold under the trade name Pluronics F108 by BASF, Ludwigshafen, Germany. Under room temperature conditions, this solution is a liquid, but when applied to warm tissue the solution forms a gel which permits the infusion of active agent into the wound tissue for a period of several days. Other formulations of interest include carboxymethyl cellulose preparations, crystalloid preparations (e.g., saline, Ringer's lactate solution, phosphate-buffered saline, etc.) and wound dressings (e.g., bandages, etc.).

The healing effects of the compounds of the present invention may be provided in a variety of instances. The solution may be applied topically to surface wound tissue in the treatment of severe burns, trauma, stasis ulcers, periodontal conditions, lacerations and other conditions. In addition, intraperitoneal wound tissue such as that resulting from invasive surgery may be treated with a composition in accordance with the present invention to accelerate healing. For example, following the surgical removal of a colon section or other tissue, the surgical plane may be coated with a solution of active agent prior to dosing the surgical site in order to accelerate internal capillary perfusion and healing. In addition, the rate of localized healing may be increased by the subdermal administration of active agent by injection or otherwise.

The invention may be better understood with reference to the accompanying example, which is intended for purposes of illustration only and should not be construed as in any sense limiting the scope of the invention as defined in the claims, appended hereto.

EXAMPLE

Male Sprague Dawley rats, 12 weeks old, were obtained from Simonsen Laboratories, Gilroy, Calif. On the day of surgery, the rats received intramuscular ketamine/rompum anesthesia prior to preparation for surgery. The rats were shaved and scrubbed with betadine. Four 2×2 cm full thickness dermal wounds were created on the dorsal surface of the rat. Following excision of the skin, the size of the wound was outlined on a glass slide and the medicament was administered in 100 μl Hydron solution comprising 10% Hydron, 1% polyethylene glycol (MW 400) and 60% ethanol. The test materials were administered in a randomized fashion; all materials were tested at 3 μg/wound and analogs 2 and 3 were also evaluated at 10 μg/wound. Controls were treated with vehicle only.

After administration of the materials, the rats were bandaged and allowed to recover from anesthesia. At days 2, 5, 6, 8 and 10, the area of the skin wounds were measured under methoxyflurane anesthesia (commercially available as Metofane from Pittman-Moore, Mundelein, Ill.). The area of the wound was determined by: (1) tracing the wound shape onto graph paper (1×1 mm squares); (2) cutting out the shape; (3) weighing the paper and comparing the weight with a 2×2 cm paper cutout; and (4) counting the number of squares.

Figure 2:
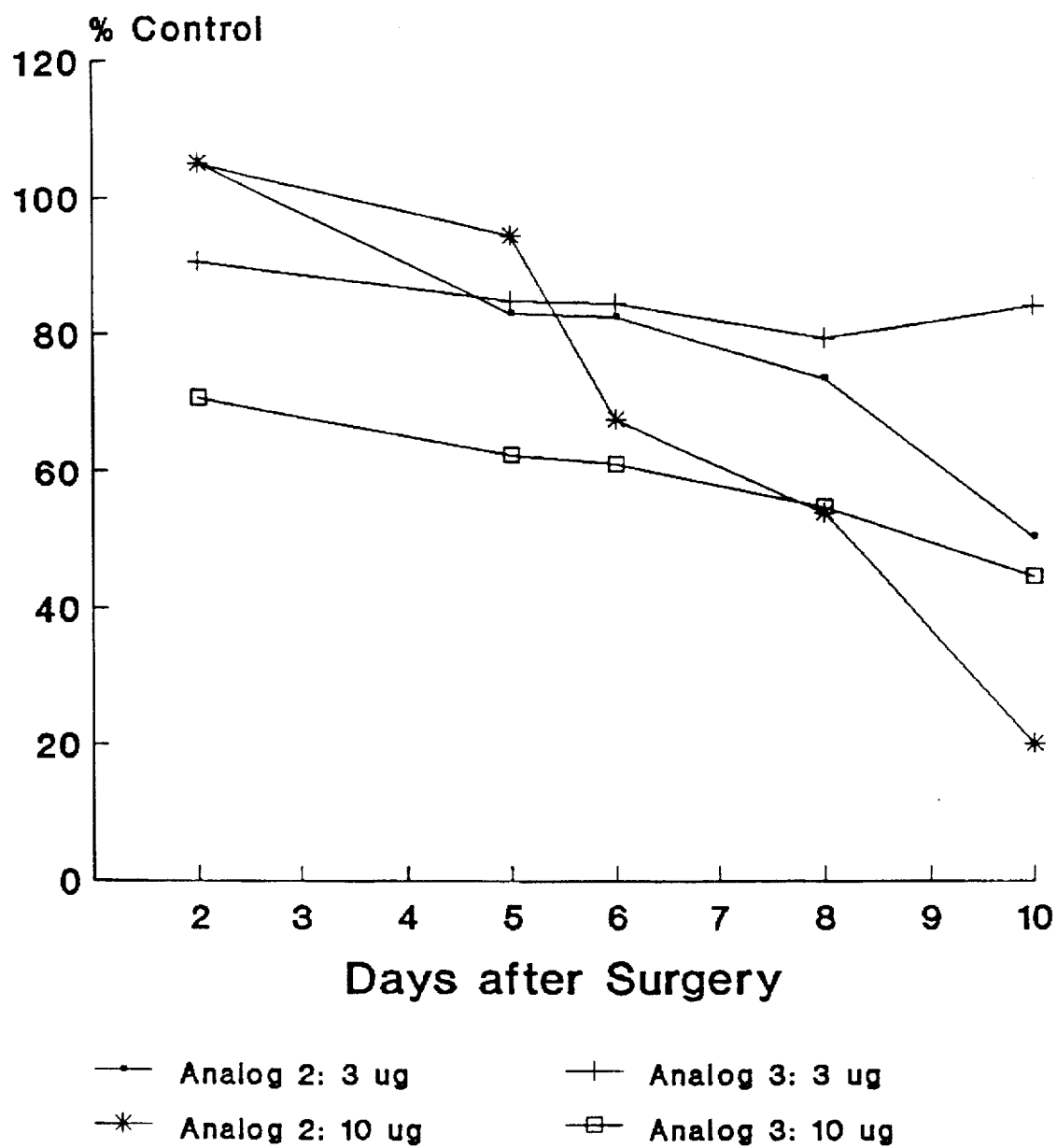
Figure 3:
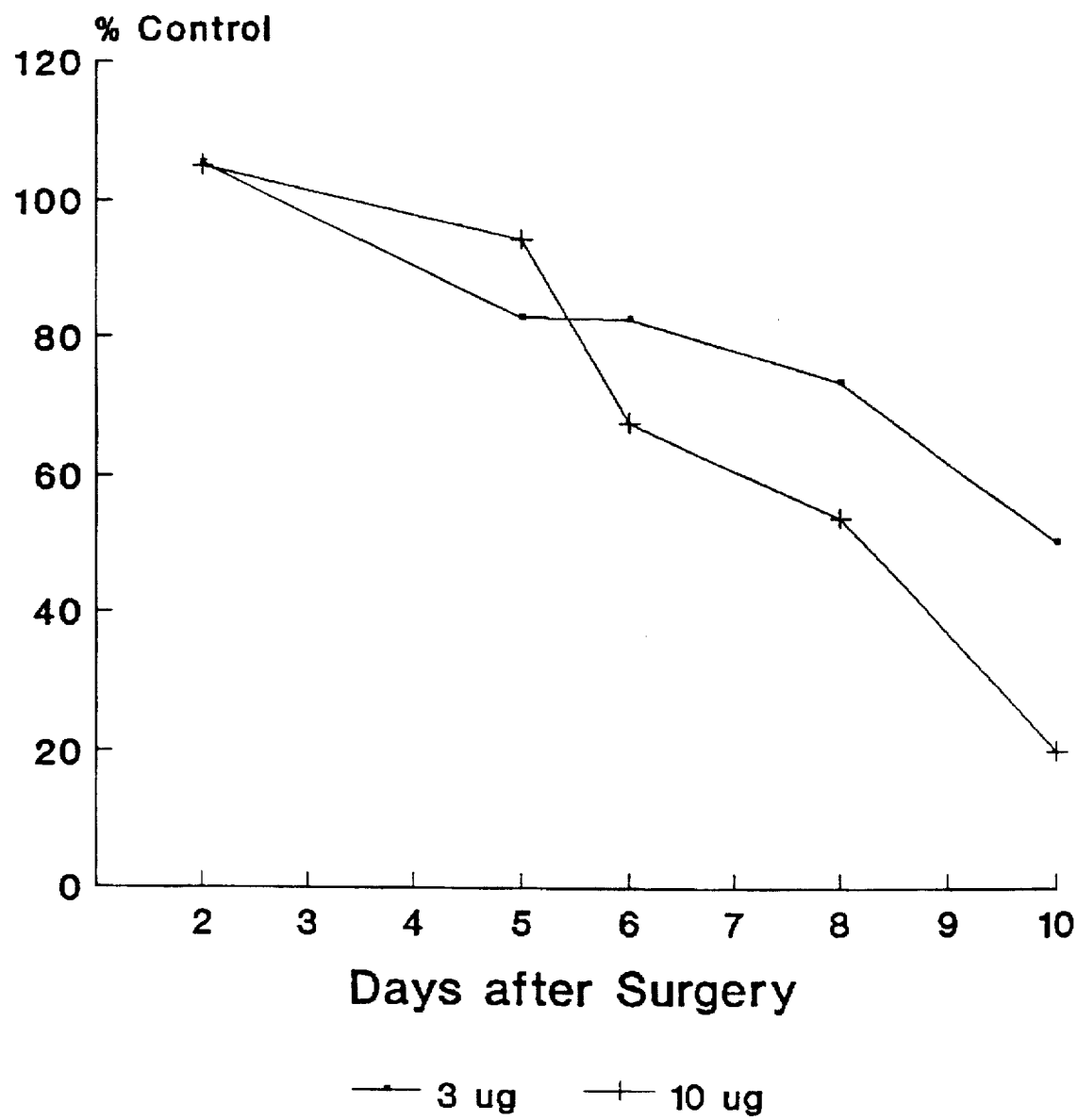

As illustrated in the drawings, wound closure was substantially accelerated relative to the control animals when the test animals were treated with Analogs 1 (FIG. 1), 2 and 3 (FIG. 2) in accordance with general formula I. The figures illustrate the percent increase in wound closure relative to a vehicle-treated control. Surprisingly, administration of Analog 4 (Sar-Arg-Val-Tyr-Ile-His-Pro-Phe [SEQ ID NO:6]) which is outside the scope of general formula I because $R^4$ is Sar did not accelerate wound repair (FIG. 1); this analog has been reported to have full affinity and activity for angiotensin II receptor, but is resistant to cleavage by aminopeptidase [Mendelsohn, F A O et al. (1984) Autoradiographic localization of angiotensin II receptors in rat brain. Proc. Nat. Atari. Sci. USA 81:1575; Israel, A. et al. (1984) Quantitative determination of angiotensin II binding sites in rat brain and pituitary gland by autoradiography. Brain Res. 322:341–5; Harding, J W and D Felix (1987) Effects of aminopeptidase inhibitors amastatin and bestatin on angiotensin-evoked neuronal activity in rat brain. Brain Res. 424:299–304]. FIG. 3 illustrates the greater efficacy of the 10 μg relative to the 3 μg dosage.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A method of accelerating wound healing in mammalian tissue, comprising applying to a wound an amount effective to accelerate wound healing of a compound of general formula I $R^1-R^2-R^3-R^4-R^5-R^6-R^7$ in which $R^1$ is a group of formula $X-R^A-R^B-$, wherein X is H or a one to three peptide group and $R^A$ and $R^B$ together form a peptide bond labile to aminopeptidase A cleavage;

$R^2$ is selected from the group consisting of Val, Ala, Leu, Ile, Gly, Pro, Aib, Acpc and Tyr;

$R^3$ is selected from the group consisting of Tyr, Thr, Ser and azaTyr;

$R^4$ is selected from the group consisting of Ile, Ala, Leu, Val and Gly;

$R^5$ is selected from the group consisting of His and Arg;

$R^6$ is selected from the group consisting of Pro and Ala; and $R^7$ is selected from the group consisting of Phe, Phe(Br) and Tyr, excluding the sequence Asp-Arg-Val-Tyr-Ile-His-Pro-Phe [SEQ ID NO:1].

2. A method according to claim 1, wherein X is H; $R^A$ is selected from the group consisting of Asp, Glu, Asn, Acpc, Ala, Me²Gly, Pro, Bet, Glu(NH₂), Gly, Asp(NH₂) and Suc; and $R^B$ is selected from the group consisting of Lys, Arg, Ala and Orn.

3. A method according to claim 2, wherein $R^A$ is Asp or Glu and $R^B$ is Arg or Lys.

4. A method according to claim 1, wherein the compound of general formula I has the formula H-R^A-R^B-R²-Tyr-R⁴-His-Pro-Phe       [SEQ ID NO:2]

in which $R^A$ is selected from the group consisting of Asp, Glu, Asn, Acpc, Ala, Me²Gly, Pro, Bet, Glu(NH₂), Gly, Asp(NH₂) and Suc; $R^B$ is selected from the group consisting of Lys, Arg, Ala and Orn; and $R^2$ and $R^4$ are as previously defined.

5. A method according to claim 4, wherein $R^A$ is Asp or Glu and $R^B$ is Arg or Lys.

6. A method according to claim 1, wherein the compound of general formula I is selected from the group consisting of Asp-Arg-Val-Tyr-Val-His-Pro-Phe [SEQ ID NO:3], Asn-Arg-Val-Tyr-Val-His-Pro-Phe [SEQ ID NO:4] and Ala-Pro-Gly-Asp-Arg-Ile-Tyr-Val-His-Pro-Phe [SEQ ID NO:5].

7. A method according to claim 1, wherein the compound of general formula I is administered in a matrical or micellar solution.

8. A method according to claim 1, wherein the compound of general formula I is administered at a concentration of at least 30 micrograms per milliliter in a suitable carrier or diluent.

9. A method according to claim 8, wherein the carrier or diluent is selected from semi-solid polyethylene glycol polymer, carboxymethyl cellulose preparations and crystalloid preparations.

10. A method according to claim 1, wherein the compound of general formula I is administered in conjunction with a wound dressing.

11. A composition for accelerating wound healing in mammalian tissue, comprising a suitable carrier or diluent and an amount effective to accelerate wound healing of compound of general formula I

R¹-R²-R³-R⁴-R⁵-R⁶-R⁷ in which $R^1$ is a group of formula

X-R^A-R^B-, wherein X is H or a one to three peptide group and $R^A$ and $R^B$ together form a peptide bond labile to aminopeptidase A cleavage;

$R^2$ is selected from the group consisting of Val, Ala, Leu, Ile, Gly, Pro, Aib, Acpc and Tyr;

$R^3$ is selected from the group consisting of Tyr, Thr, Ser and azaTyr;

$R^4$ is selected from the group consisting of Ile, Ala, Leu, Val and Gly;

$R^5$ is selected from the group consisting of His and Arg;

$R^6$ is selected from the group consisting of Pro and Ala; and $R^7$ is selected from the group consisting of Phe, Phe(Br) and Tyr, excluding the sequence Asp-Arg-Val-Tyr-Ile-His-Pro-Phe [SEQ ID NO:1].

12. A composition according to claim 1, wherein X is H; $R^A$ is selected from the group consisting of Asp, Glu, Asn, Acpc, Ala, Me²Gly, Pro, Bet, Glu(NH₂), Gly, Asp(NH₂) and Suc; and $R^B$ is selected from the group consisting of Lys, Arg, Ala and Orn.

13. A composition according to claim 12, wherein $R^A$ is Asp or Glu and $R^B$ is Arg or Lys.

14. A composition according to claim 11, wherein the compound of general formula I has the formula H-R^A-R^B-R²-Tyr-R⁴-His-Pro-Phe       [SEQ ID NO:2]

in which $R^A$ is selected from the group consisting of Asp, Glu, Asn, Acpc, Ala, Me²Gly, Pro, Bet, Glu(NH₂), Gly, Asp(NH₂) and Suc; $R^B$ is selected from the group consisting of Lys, Arg, Ala and Orn; and $R^2$ and $R^4$ are as previously defined.

15. A composition according to claim 14, wherein $R^A$ is Asp or Glu and $R^B$ is Arg or Lys.

16. A composition according to claim 11, wherein the compound of general formula I is selected from the group consisting of Asp-Arg-Val-Tyr-Val-His-Pro-Phe [SEQ ID NO:3], Asn-Arg-Val-Tyr-Val-His-Pro-Phe [SEQ ID NO:4] and Ala-Pro-Gly-Asp-Arg-Ile-Tyr-Val-His-Pro-Phe [SEQ ID NO:5].

17. A composition according to claim 11, wherein the compound of general formula I is administered in a matrical or micellar solution.

18. A composition according to claim 11, wherein the compound of general formula I is administered at a concentration of at least 30 micrograms per milliliter.

19. A composition according to claim 11, wherein the carrier or diluent is selected from semi-solid polyethylene glycol polymer, carboxymethyl cellulose preparations and crystalloid preparations.

20. A composition according to claim 11, wherein the compound of general formula I is administered in conjunction with a wound dressing.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Asp Arg Val Tyr Ile His Pro Phe
    1                    5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( D ) TOPOLOGY: linear (ii) MOLECULE TYPE: peptide (xi) SEQUENCE DESCRIPTION: SEQ ID NO:2:

Xaa Xaa Xaa Tyr Xaa His Pro Phe
1               5

(2) INFORMATION FOR SEQ ID NO:3:

(i) SEQUENCE CHARACTERISTICS:
      (A) LENGTH: 8 amino acids
      (B) TYPE: amino acid
      (D) TOPOLOGY: linear (ii) MOLECULE TYPE: peptide (xi) SEQUENCE DESCRIPTION: SEQ ID NO:3:

Asp Arg Val Tyr Val His Pro Phe
1               5

(2) INFORMATION FOR SEQ ID NO:4:

(i) SEQUENCE CHARACTERISTICS:
      (A) LENGTH: 8 amino acids
      (B) TYPE: amino acid
      (D) TOPOLOGY: linear (ii) MOLECULE TYPE: peptide (xi) SEQUENCE DESCRIPTION: SEQ ID NO:4:

Asn Arg Val Tyr Val His Pro Phe
1               5

(2) INFORMATION FOR SEQ ID NO:5:

(i) SEQUENCE CHARACTERISTICS:
      (A) LENGTH: 11 amino acids
      (B) TYPE: amino acid
      (D) TOPOLOGY: linear (ii) MOLECULE TYPE: peptide (xi) SEQUENCE DESCRIPTION: SEQ ID NO:5:

Ala Pro Gly Asp Arg Ile Tyr Val His Pro Phe
1               5                   10

(2) INFORMATION FOR SEQ ID NO:6:

(i) SEQUENCE CHARACTERISTICS:
      (A) LENGTH: 8 amino acids
      (B) TYPE: amino acid
      (D) TOPOLOGY: linear (ii) MOLECULE TYPE: peptide (xi) SEQUENCE DESCRIPTION: SEQ ID NO:6:

Xaa Arg Val Tyr Ile His Pro Phe
1               5